United States Patent
Schaumburg et al.

(10) Patent No.: US 9,827,296 B2
(45) Date of Patent: Nov. 28, 2017

(54) AEROGEL COMPOSITIONS

(71) Applicant: EnCoat ApS, Copenhagen (DK)

(72) Inventors: Kjeld Schaumburg, Herlev (DK); Eva Wallstrom, Copenhagen (DK)

(73) Assignee: EnCoat ApS, Copenhagen (DK)

( * ) Notice: Subject to any disclaimer, the term of this patent is extended or adjusted under 35 U.S.C. 154(b) by 0 days.

(21) Appl. No.: 14/156,313

(22) Filed: Jan. 15, 2014

(65) Prior Publication Data

US 2014/0194551 A1    Jul. 10, 2014

Related U.S. Application Data

(63) Continuation of application No. 12/742,649, filed as application No. PCT/EP2008/065417 on Nov. 12, 2008, now abandoned.

(60) Provisional application No. 60/987,221, filed on Nov. 12, 2007, provisional application No. 61/059,353, filed on Jun. 6, 2008.

(30) Foreign Application Priority Data

Nov. 12, 2007  (DK) ................................ 200701594
Jun. 6, 2008  (EP) ..................................... 08157766

(51) Int. Cl.

| | |
|---|---|
| *C12N 9/00* | (2006.01) |
| *A61K 38/48* | (2006.01) |
| *B01J 13/00* | (2006.01) |
| *C09D 5/16* | (2006.01) |
| *C09D 7/12* | (2006.01) |
| *A61K 9/48* | (2006.01) |
| *C08K 3/22* | (2006.01) |
| *C08K 3/34* | (2006.01) |

(52) U.S. Cl.
CPC .............. *A61K 38/482* (2013.01); *A61K 9/48* (2013.01); *B01J 13/0091* (2013.01); *C09D 5/1637* (2013.01); *C09D 5/1687* (2013.01); *C09D 7/1291* (2013.01); *C08K 3/22* (2013.01); *C08K 3/34* (2013.01)

(58) Field of Classification Search
CPC ..... A61K 38/482; A61K 9/48; B01J 13/0091; C08K 3/22; C08K 3/34; C09D 5/1637; C09D 5/1687; C09D 7/1291; C09D 5/1612
See application file for complete search history.

(56) References Cited

U.S. PATENT DOCUMENTS

| | | | |
|---|---|---|---|
| 5,260,066 A | 11/1993 | Wood et al. ................... | 424/447 |
| 6,303,290 B1 | 10/2001 | Liu et al. | |
| 6,777,223 B2* | 8/2004 | Xu ............................. | 435/262.5 |
| 6,994,842 B2 | 2/2006 | Lee et al. | |
| 2001/0026802 A1 | 10/2001 | Price et al. | |
| 2002/0094318 A1 | 7/2002 | Lee et al. | |
| 2003/0148268 A1 | 8/2003 | Fischetti et al. ................... | 435/5 |
| 2003/0213505 A1 | 11/2003 | Price et al. | |
| 2004/0197414 A1 | 10/2004 | Ahola et al. ................... | 424/489 |
| 2005/0147579 A1* | 7/2005 | Schneider et al. ......... | 424/78.09 |
| 2007/0225515 A1 | 9/2007 | Blum | |
| 2010/0016502 A1 | 1/2010 | Renthrop et al. | |

FOREIGN PATENT DOCUMENTS

| | | | |
|---|---|---|---|
| DE | 102004008931 | | 9/2004 |
| EP | 1825752 | | 8/2007 |
| EP | 1882722 | | 1/2008 |
| WO | WO 99/64504 | * | 12/1999 |
| WO | WO02074868 A1 | | 9/2002 |
| WO | WO02080977 A1 | | 10/2002 |
| WO | 03096863 | | 11/2003 |
| WO | WO 2006063176 A2 | | 6/2006 |

OTHER PUBLICATIONS

Maury et al. Macromolec. Biosci. (2001) 1: 119-125.*
Novak et al. Chem. Mater. (1994) 6: 272-286.*
Pierre et al. Chem. Rev. (2002) 102: 4243-5265.*
Machine translation of WO 99/64504 downloaded from the EPO Feb. 8, 2016.*
I. Gill and A. Ballesteros, 'Bioencapsulation within synthetic polymers (Part I): sol-gel encapsulated biological', Tibtech 18: 282-296 (2000).
Y. Wie et al., 'Encapsulation of enzymes in mesoporous host materials via the nonsurfactant-templated sol-gel process', Materials Letters 44: 6-11 (2000).
S. Radin et al., ,Silica sol-gel for the controlled release of antibiotics. I. Synthesis, characterization, and in vitro release, J. Biomed. Mater. Res. 57: 313-320 (2001).
Falaize et al. J. Am. Ceram. Soc. (1999) 82(4): 969-976.
Definition of "film" downloaded from http://dictionary.com/browse/film on Nov. 9, 2012.
Avnir (Chem. Mat. (1994) 6: 1605-1614.
Radin et al. Biomaterials (2992) 23(15): 3113-22.

* cited by examiner

*Primary Examiner* — Susan Hanley
(74) *Attorney, Agent, or Firm* — Fish & Richardson P.C.

(57) ABSTRACT

The present invention relates to gel compositions comprising at least one entrapped active component.

11 Claims, No Drawings

AEROGEL COMPOSITIONS

CROSS REFERENCE TO PRIOR APPLICATIONS

This is a Continuation application of U.S. Ser. No. 12/742,649 filed on Aug. 30, 2010, which is a U.S. National Phase application under 35 U.S.C. §371 of International Patent Application No. PCT/EP2008/065417, filed Nov. 12, 2008, and claims the priority of Danish Patent Application No. PA200701594, filed Nov. 12, 2007; U.S. Provisional Application No. 60/987,221, filed Nov. 12, 2007; European Patent Application No. 08157766.0, filed Jun. 6, 2008; and U.S. Provisional Application No. 61/059,353, filed Jun. 6, 2008, all of which are incorporated by reference herein. The International Application published in English on May 22, 2009 as WO 2009/062975 under PCT Article 21 (2).

FIELD OF THE INVENTION

The present invention relates to the field of gels and the use of gels as means for storage and controlled release of component therefrom.

BACKGROUND OF THE INVENTION

Sol-gel chemistry has been used for many years. Most research has been directed towards inorganic gels created by hydrolysis of metal alkoxides. NASA has developed aerogels where the strength and the heat insulation properties of these materials have been optimized. Many other scientists have been reporting on the use of gels and aerogels for control of drug delivery. Here the gel performs the role as a sponge absorbing medically active compounds for later slow release. The process of interest is here diffusion out of the inert gel material. Yet another direction of research has been to encapsulate large molecules like proteins or even live bacteria or cells into the gel network. It has been found that in many cases the enzymes encapsulated in the gel retain their activity. In special cases as observed with Lipases they may even display significantly enhanced activity when located in the gel network. The gel is thus used as a bioreactor where the enzyme is staying fixed while the reactants and the products diffuse in and out of the very open gel network. Also in these last two situations it is important that the gel is strong and that it can retain its properties during the processes.

Aerogel particles have been proposed for use in controlled release of pharmaceuticals, see e.g. U.S. Pat. No. 6,994,842 B2.

Active compounds are a necessity for protection against biological growth in the coatings field. Due to environmental restrictions against traditional biocides and fungicides the need for more environmentally acceptable solutions is growing. Even though attempts to use enzymes and/or other organic molecules can be found in literature the success is restricted. Incorporating this type of molecules in a paint or coating is not an easy task.

In paints containing enzymes such as proteases the waterborne systems may have stability problems since sedimentation during storage result in a pigment and binder precipitate and a water enzyme liquid phase. During storage the enzyme react in an autodegradation whereby the enzyme activity is significantly reduced. For this purpose it would be highly significant if the enzyme could be prevented from degradation during storage.

There is also a need to keep the active compound on the coating surface in an effective dosage to get a proper protection.

Furthermore it must be considered that different types of coatings depending on the application probably will need different solutions to the dosage problem.

Aerogels have been known to be useful as additives in paint formulations since they among other properties may introduce thixotropic properties. This property allows industrial spraying of thicker films of good quality. WO 2002/074868 discloses thixotropic paint formulations comprising silica aerogel.

SUMMARY OF THE INVENTION

In order to overcome the above-mentioned limitations of the known compositions for entrapment, storage and subsequent controlled release of an active component, the present invention provides a composition comprising a gel wherein is entrapped at least one active component such that release of said at least one active component from said composition is substantially caused by degradation of said gel.

In one aspect the present invention relates to a composition comprising an aerogel wherein is entrapped at least one active component such that release of said at least one active component from said composition is substantially caused by degradation of said aerogel.

In one aspect the present invention relates to a composition comprising an wet gel wherein is entrapped at least one active component such that release of said at least one active component from said composition is substantially caused by degradation of said gel. The gel is prepared in a solvet mixture identical in composition to the paint in which it is planned to be incorporated.

In one embodiment of the invention said at least one active component substantially is not liberated from said composition by diffusion out of said composition.

DEFINITIONS

The term sol as used herein means a solution of various reactants that are undergoing hydrolysis and condensation reactions. The molecular weight of the oxide species produced continuously increases. As these species grow, they may begin to link together in a three-dimensional network.

The term alcogel as used herein means a wet gel which can be removed from its original container and can stand on its own. An alcogel consists of two parts, a solid part and a liquid part. The solid part is formed by the three-dimensional network of linked oxide particles. The liquid part (the original solvent of the Sol) fills the free space surrounding the solid part. The liquid and solid parts of an alcogel occupy the same apparent volume.

The term supercritical fluid as used herein means a substance that is above its critical pressure and critical temperature. A supercritical fluid possesses some properties in common with liquids (density, thermal conductivity) and some in common with gases (fills its container, does not have surface tension).

The term aerogel as used herein means what remains when the liquid part of an alcogel is removed without damaging the solid part. Removal of the liquid part can be achieved by e.g. supercritical extraction. If made correctly, the aerogel retains the original shape of the alcogel and at least 50% (typically >85%) of the alcogel's volume.

The term xerogel as used herein means what remains when the liquid part of an alcogel is removed by evaporation, or similar methods. Xerogels may retain their original shape, but often crack. The shrinkage during drying is often extreme (~90%) for some xerogels.

The term cryogel as used herein means what remains when an alcogel is frozen and the previously liquid part of the alcogel is removed by evaporation keeping the alcogel frozen all the time. Cryogels may retain their original shape, but often crack. The shrinkage during drying may be substantial for some cryogels. Addition of suitable surfactants in the alcogel may relieve this problem.

The term substantially as used herein means considerably such as when expressed as a percentage at least 25%, such as at least 40%, such as at least 50%, such as at least 75%, such as at least 85%, such as at least 95%. For instance "release of X is substantially caused by degradation of said gel" means that release of X is caused considerably by degradation of said gel.

DETAILED DESCRIPTION OF THE INVENTION

The present invention reverse in a sense the priorities and thereby providing a new area of applications. In the invention molecules are entrapped in the gel, e.g. during the SOL-GEL process. Since pores in the gel frequently will be between 1 and 20 nm the network is capable of encapsulating large molecules where the gel network creates bottleneck for passing. Other smaller molecules may be retained by the strong interaction with the cavity walls in the gel. Thus the molecules claimed to be of interest for the invention are molecules displaying no pronounced tendency to leach out of the gel.

This encapsulation of organic molecules set the loaded gels apart from the first class of applications mentioned above. The focus on molecules permanently entrapped in the gel set the invention apart from the second class. The entrapment still concurs with the third class. The loaded gel prepared in the liquid form or as an aerogel, cryogel or xerogel is designed by its chemical composition to be degradable under the conditions where it is planned to be used. The degradation may be chemical—as it happens with hydrolysis in water—where the pH of the water strongly influences the hydrolysis rate of metal alkoxy based gels. The degradation may however be purely mechanical as it is occurring when grains of the gel are present at a surface where friction wear down the grains.

By this design the gel differs markedly from the classes 2 and 3 and in most cases from class 1 since optimization of strength occur for a completely different set of criteria in the space research.

The encapsulation of molecules in the gel may have a number of effects to be exploited in the present invention changing the release profile during gel decomposition.

They may be protected against degradation as an effect of their spatial confinement They may be showing increased thermal stability due to their interaction with the gel structure They may show improved stability towards irradiation stability due to their interaction with the gel structure Their release will be controlled by the degradation of the gel lattice Molecules may be functionalized in such a manner that the functionalized molecule can be acting as an active component in the network formation. The covalent binding to the gel network may result in a release of the active compound still linked to fragments of the gel network.

Often it is a problem to disperse a hydrophilic substance in a hydrophobic solvent and visa verse. By inclusion of the substance in the gel it is possible to control the distribution in the solvent by tailoring the polarity of the gel.

Hydrophilic biomolecules may be included in a hydrophobic gel thereby ensuring their homogeneous distribution in a hydrophobic solvent.

By production of an aerogel, cryogel or xerogel the release will be determined by the grain size and composition of the Gel.

Many variations of the gel structure are possible in order to control degradation. They include mixing of various metal alkoxides, introduction of alkyl or aryl substituents on some of the alkoxides The gel properties may also be modified by introduction of polymers as part of the original sol. Subsequently they will be entrapped and end up as part of the gel network.

A manufacturer may optimize a composition including gel including one entrapped species. Replacement of the entrapped species with another does not require renewed optimization since the gel retains its physical properties independent of the entrapped species.

Several gels with different entrapped species may be mixed as powders to obtain a desirable effect.

Several active compounds may be incorporated in the same sol/gel since the species are entrapped individually their effects are not affected by potential mutual interactions The sol gel process may be carried ouL in such a manner that two or more different compounds are entrapped in different regions of the same gel. This requires the gelation process to be interrupted for each addition of an entrapped species.

Two or more compounds may be entrapped and selected so that upon their release they can chemically react whereby new products are formed. An enzyme and a substrate may serve as an example. The reaction products may be small highly reactive molecules The gels prepared according to this invention are foreseen to have application in Coatings in general, e.g. paint, ink, lacquer products where the film thickness warrants the integration of gel structures.

In surfaces on medical devices

In plast composites

The known property as a thixotropic component in coatings may be combined with the properties obtained by this invention As a consequence of the regulations on chemicals and biocides derivatives of active molecules are considered as new species requiring individual risk assessments. By entrapment the molecules are not chemically modified but their effects are controlled. This may result in considerable time and financial savings.

Silica aerogels may be prepared according to traditional microparticle sol-gel processing.

Solvent Based Coatings.

Even though the use of solvent-based coatings has been restricted it is still an area of importance.

Introducing an aerogel in a solvent-based paint has the following effects:
  Structure is introduced into the wet paint at low shear rates
  The degradation rate of the coating increases
  Water up-take is increased compared to coatings without aerogels, but still low due to the fact that solvent-based coatings are normally very dense
  The release of an active substance can be controlled as the release will be related to the degradation effect As possible application areas traditional solvent-based paints for outdoor protection can be mentioned. It should be acknowledged that the choice of the optimal binder systems used is important. The above concept based on degradation over time can mainly be used on materials, where the degradation time is acceptable. One example is coatings for wood (alkyds have always degraded due to the climate (sun and rain)), roofs, etc.

It should be mentioned that during the grinding process of the paint/coating there will be a small not intentional release of the active compound from the aerogel due to mechanical forces applied to the surface of the formulation. The proportion of active compound release is not expected to be significant as the aerogel particles aimed for in the paint still have a small surface to volume ratio.

Water-Borne Coatings.

There is a demand for water-borne coatings in general.

Water-borne coatings are used on a large scale for architectural paints, wood protection etc. But at the same time water-borne coatings are used on a very small scale in the yacht market and heavy-duty products. As an example an anti-fouling yacht paint can be mentioned.

To achieve a desired polishing rate the coating has to degrade due to mechanical friction.

The parameters that influence the polishing rate is the choice of binders, their concentration as well as the choice of pigments/fillers and their concentration.

Introducing a gel in a water-borne anti-fouling paint has the following effects:
  The polishing rate of the coating increases
  Water up-take is increased significantly compared to coatings without aerogels
  The water up-take can be reduced in several ways:
  Introducing a hydrophobic agent, which probably is not enough on its own
  Changing the gel composition and thus making the film more water resistant.

It is relevant to reduce water up-take to achieve a commercially acceptable anti-fouling paint.

It should be mentioned that water-borne coatings are very important today. Outdoors it is crucial to achieve protection against bio-films on wood, houses, roofs etc. But also indoors problems with bacteria and fungi are essential especially in wet rooms.

In another aspect the present invention provides an gel modified by an interpenetrating network of a polymer. The polymer is chosen to fulfil the criteria:
1. it is water soluble or dispersible
2. it is compatible with the formation of the gel network
3. it is actively promoting the molecular dispersion of for example a biomolecule, e.g. an enzyme, in the gel network. If this is not possible the polymer should be acting as a neutral component not hampering the dispersion of the biomolecule, e.g. an enzyme, in the gel network.
4. The interpenetrating polymer aerogels network should result in particles that may be dispersed in the organic phase of the liquid paint
5. The polymer should reduce the water uptake or water uptake rate in the aerogel in such a manner that the polishing rate for the paint film is reduced.
6. The molecular weight of the polymer should be so large that physical entanglement in the aerogel leads to an efficient immobilization. At the same time the polymer molecular weight should not exceed the limit where its introduction in the gel-forming step would result in an unacceptable increase of the viscosity.

As a nonexclusive criterion it is relevant to include polymers where the environmental and toxicological clearances already have been obtained. Examples of such substances are polyethyleneglycols, polylactic acid, polyvinylalkohol, polyvinylpyrrolidone, poly-lysine, heparins, polyhyaluronic acid, polysaccharides and many more.

The gel is typically silica based. The silicon may fully or partly be replaced by other tri- or tetra-valent metal ions.

According to another aspect of the present invention it is possible to store, preserve and release enzymes from an gel used as a component in a surface film. In the case of biofouling a bacterial film is rapidly formed on the surface. The success of the aerogel containing enzyme rely on the controlled availability of sufficient large quantities of enzyme at a give time to impede or reduce the evolution of the biofilm and the settlement of algae, mussels and barnacles in the bacteria film.

Various enzymes may be suitable as active components in the composition of the present invention. In one embodiment the at least one enzyme or protein comprises at least one enzyme selected from the group consisting of hemicellulolytically active enzymes, amylolytically active enzymes and/or cellulolytically active enzymes.

In another embodiment the one or more bioactive agent(s) comprises endopeptidases.

In one embodiment the endopeptidase(s) comprises a Subtilisin (EC 3.4.21.62). The Subtilisin (EC 3.4.21.62) has the following characteristics: (i) optimum activity at a pH in the range of about 7-10, and (ii) optimum activity at a temperature in the range of about 55-65° C. The Subtilisin (EC 3.4.21.62) is in one embodiment Alcalase.

In one embodiment the hemicellulolytically active enzyme(s) is selected from the group consisting of Endo-1, 4-beta-xylanase (E.C. 3.2.1.8), Xylan endo-1,3-beta-xylosidase (E.C. 3.2.1.32). Glucuronoarabinoxylan endo-1,4-beta-xylanase (E.C. 3.2.1.136), Betamannosidase (E.C. 3.2.1.25), Mannan endo-1,4-beta-mannosidase (5 E.C. 3.2.1.78) and Mannan endo-1,6-beta-mannosidase (E.C. 3.2.1.101). In another embodiment the hemicellulolytically active enzyme is a xylanase. In one embodiment the xylanase is an endo-1,4-beta-xylanase (E.C. 3.2.1.8).

The amylolytically active enzyme(s) can in one embodiment be an amylase.

In another embodiment the one or more amylolytically active enzyme(s) is selected from the group consisting of α- and β-amylases, amyloglucosidases (E.C. 3.2.1.3), pullulanases, α-1,6-endoglucanases, α-1,4-exoglucanases and isoamylases.

The one or more amylolytically active enzyme(s) can also be amyloglucosidase.

In one embodiment the amyloglucosidase is an 1,4-alpha-glucosidase.

In one embodiment the anti-fouling composition agent comprises one or more gel(s) and at least one xylanase and at least one amyloglucosidase.

In another embodiment the anti-fouling composition agent comprises one or more gel(s) and at least one endo-1,4-beta-xylanase (E.C. 3.2.1.8) and at least one 1,4-alpha-glucosidase (E.C. 3.2.1.3).

In yet another aspect the present invention provides an aerogel comprising bacteriophages. Bacteriophages are much smaller than the bacteria they destroy—usually between 20 and 200 nm in size.

They have been used for over 60 years as an alternative to antibiotics in the former Soviet Union and Eastern Europe. Bacteriophages are viruses targeting and preying on bacteria. In this sense they are universally present in low concentrations. They are highly specific and therefore constitute no danger for species outside the family of bacteria for which they are targeted.

Bacteriophages are not capable of multiplying unless they are prying on the bacteria they target. They are seen as a possible therapy against multi drug resistant strains of many bacteria. As complex proteins they themselves can naturally be attacked and consumed by other organisms.

From a suspension containing Bacteriophages they may be immobilized by conversion of the suspension to a hydrogel. Several patents and articles describe this procedure. Once encaged in the gel network the Bacteriophages are restricted in their motion and they cannot get contact to the bacteria the pray on. Conversely the organisms that might consume the Bacteriophages cannot get access to them due to the gel network. The hydrogel network may by a suitable treatment be disintegrated to small fragments the size of micrometers. Still the bacteriophages will be encapsulated in these fragments. These small fragments may be distributed in a paint formulation and be applied to create a coating. During degradation (with antifouling paint it will be polishing rate) of the paint bacteriophages will slowly be released. If a biofilm with the target family of bacteria grows on the surface of the paint the bacteriophages will rapidly attack the bacteria and multiply as long as the family of bacteria is present on the surface. The constant release of a low dose of bacteriophages will stabilize this scenario and prevent the formation of colonies of bacteria of the selected type. In August, 2006 the US Food and Drug Administration (FDA) approved using bacteriophages on cheese to kill the *Listeria monocytogenes* bacteria, giving them GRAS status (Generally Recognized As Safe). In July 2007, the same bacteriophages were approved for use on all food products.

From biological studies of early settlement on clean surfaces it is known, that the colonization of a given surface typically is performed by a limited number of bacteria. The species performing this function may vary in different regions on the globe. It is completely feasible to use a cocktail of several relevant bacteriophages in the formation of the hydrogel. Hereby the attack on the biofilm bacteria will be on all the relevant bacteria and the resulting destruction of the biofilm more complete.

Non-limiting examples of lytic bacteriophages suitable for used according to the present invention is λ phage-lysogen, T2 phage, T4 phage, T7 phage. T12 phage, R17 phage, M13 phage, MS2 phage, G4 phage, P1 phage, P2 phage, Phi X 174 phage, N4 phage, Φ6 phage, Φ29 phage and 186 phage.

For the practical use of the invention within paints based on organic solvents it will not suffice to create a hydrogel. Following normal procedures the gel particles should be suspended in the organic phase of the paint. Here hydrogels are a poor choice since they will be polar and incompatible with the organic phase. For most applications the conversion of the hydrogel to an aerogel/cryogel will be required. After this conversion the dried gel can be suspended in the organic phase. This ensures a better distribution in the coating film and a better storage stability.

It is central to this invention that it is possible to convert the hydrogel into aero/cryogel without significant losses in bacteriophage activity.

The present invention relates to the following aspects:

1. Use of a gel containing Bacteriophages as a component of an antifouling paint or other antibacterial paint/lacquer and coatings
2. preparation of an aerogel containing Bacteriophages as a component of an antifouling paint and coating
3. preparation of a cryogel containing Bacteriophages as a component of an antifouling paint and coating
4. preparation of a xerogel containing Bacteriophages as a component of an antifouling paint and coating
5. preparation of an aerogel/cryogel/xerogel containing Bacteriophages that may be released in an active form from the gel.

The invention does not chemically modify the bacteriophages. Therefore they introduce no new substances to the environment.

The gel forming substances has been chosen to be based on metal oxides benign to the organisms and the environment.

EXAMPLES

Example 1

Enzymes Incorporated in a Silica Aerogel for Solvent-Based Paints and Coatings 1) 57.4 g TMOS (Tetramethyl orthosilicate 98% from Aldrich) and 229.2 g Methanol (Methanol reagent PH. EUR. from Bie & Berntsen) was mixed on a magnetic stirrer in a 1 L Erlenmeyer flask for 15 minutes.
2) 200 mL Esperase solution (HPF from Novozymes) was dialysed and freeze dried. There was obtained 18.40 g dry enzyme, which was dissolved quickly (about 5 minutes) in 60 mL milli-Q water and the viscous solution was added drop wise to 1) during mixing. The solution was mixed for additionally 15 minutes.
3) 0.933 g of ammonium hydroxide (28-30% solution from Bie & Berntsen) dissolved in 7.50 g of milli-Q water was added dropwise to 2) during mixing at full speed (1500 RPM) on the magnetic stirrer. After additionally 2 minutes of mixing, the white opaque solution was transferred into a 1 L bluecap bottle. After approx. ½ hour, the gelation took place and the obtained 410 mL gel was aged in methanol, for 24 hours at room temperature, before drying.
4) 287 g of the wet gel from 3) was cut into smaller pieces and transferred under methanol to a ½ L pressure vessel (½ L flow reactor, equipped with heating jacket and metal frits in both ends, from Thar designs). There the gel was flowed with ½ L of methanol at 0.5 mL/min. Then the temperature in the heating jacket was raised to 50° C. and the pressure raised to 100 bars, at a rate of 3 bars/min. During 8 hours at 50° C. and 100 bars, 2½ kg of $CO_2$ was flowed trough the wessel at a rate of approximately 6 mL/min measured at 10° C.

After flowing the pressure was slowly released during several hours. The weight of the supercritical dryed aerogel was 34.23 g.

Example 2

Enzymes Incorporated in a Silica Aerogel for Water-Borne Paints and Coatings 1) 28.6 g TMOS (Tetramethyl orthosilicate 98% from Aldrich) and 111.0 g Methanol (Methanol reagent PH. EUR. from Bie & Berntsen) was mixed on a magnetic stirrer in a 1 L Erlenmeyer flask for 15 minutes.
2) 0.752 g PVA (Polyvinyl alcohol, with a degree of polymerisation of 2000 and a degree of hydrolysation of 86-89 mol %, from Fluka Chemika) was wetted with 5 mL methanol and dissolved in 30 mL milli-Q water. 100 mL Esperase solution (HPF from Novozymes) was dialysed and freeze dried. Thereby 6.279 g dry enzyme was obtained, which was dissolved quickly (about 5 minutes) in the PVA solution and the obtained viscous enzyme solution was added drop wise to 1) during mixing. The solution was mixed for additionally 15 minutes.
3) 0.517 g of ammonium hydroxide (28-30% solution from Bie & Berntsen) dissolved in 3.737 g of milli-Q water was added dropwise to 2) during mixing at full speed (1500 RPM) on the magnetic stirrer. After additionally 2 minutes of mixing, the white opaque solution was transferred into a 1 L bluecap bottle. After 15 minutes the gelation took place and the obtained 200 mL gel was aged in methanol, for 24 hours at room temperature and additionally 6 days at 5° C., before drying.
4) 176.8 g of the wet gel from 3) was cut into smaller pieces and transferred under methanol to a ½ L pressure vessel (½ L flow reactor, equipped with heating jacket and metal frits in both ends, from Thar designs). There was flowed with ½ L of methanol at 0.5 mL/min. Then the temperature in the heating jacket was raised to 50° C. and the pressure raised to 100 bars, at a rate of 3 bars/min. During 8 hours at 50° C. and 100 bars, 2½ kg of $CO_2$ was flowed trough the wessel at a rate of 5-7 mL/min measured at 10° C. After flowing the pressure was slowly released during several hours. The weight of the supercritical dryed aerogel was 18.685 g.

Example 3

Antifreeze Protein Incorporated in a Silica Aerogel for Water-Borne Coatings Production of antifreeze proteins have recently been described in a patent application disclosed by its owner RUC. The antifreeze protein from *Rhagium mordax* may be taken as an example. The protein has been expressed in a microorganism. The antifreeze protein is therefore available in a solution similar to the Espherase used in example 1 and 2. The procedure for creation of aerogels incorporating antifreeze proteins will therefore substantially be the same as used for Espehrase.

Example 4

Bacteriophages Incorporated in a Silica Gel

A suspension of *Escherichia coli* T2 bacteriophages $10^{12}$ pr ml can be used as replacement for the Espherase solutions in the procedures described in example 1 and 2. The low temperature and pressure used in the formation of the aerogel is of critical importance for the viability of the bacteriophages during the aerogel formation.

Example 5

Enzymes Incorporated in a Silica Aerogel for Solvent Based Paints 1) 57.4 g TMOS (Tetramethyl orthosilicate 98% from Aldrich) and 229.2 g Methanol (Methanol reagent PH. EUR. from Bie & Berntsen) was mixed on a magnetic stirrer in a 1 L erlenmeyer flask for 15 minutes.
2) 200 mL Esperase solution (HPF from Novozymes) was dialysed and freeze dried. There was obtained 18.40 g dry enzyme, which was dissolved quickly (about 5 minutes) in 60 mL milli-Q water and the viscous solution was added drop wise to 1) during mixing. The solution was mixed for 15 minutes additionally.
3) 0.933 g of ammonium hydroxide (28-30% solution from Bie & Berntsen) dissolved in 7.50 g of milli-Q water was added dropwise to 2) during mixing at full speed (1500 RPM) on the magnetic stirrer. After additionally 2 minutes of mixing, the white opaque solution was transferred into a 1 L bluecap bottle. After a hour, the gelation took place and the obtained 410 mL gel was aged in methanol, for 24 hours at room temperature, before drying.
4) 287 g of the wet gel from 3) was cut into smaller pieces and transferred under methanol to a ½ L pressure vessel (½ L flow reactor, equipped with heating jacket and metal frits in both ends, from Thar designs). There was flowed with ½ L of methanol at 0.5 mL/min. Then the temperature in the heating jacket was raised to 50° C. and the pressure raised to 100 bars, at a rate of 3 bars/min. During 8 hours at 50° C. and 100 bars, 2½ kg of $CO_2$ was flowed trough the vessel at a rate of approximately 6 mL/min measured at 10° C. After flowing the pressure was slowly released during several hours. The weight of the supercritical dryed aerogel was 34.23 g.

Example 6

Enzymes Incorporated in a Silica Aerogel for Water Based Paints 1) 28.6 g TMOS (Tetramethyl orthosilicate 98% from Aldrich) and 111.0 g Methanol (Methanol reagent PH. EUR. from Bie & Berntsen) was mixed on a magnetic stirrer in a 1 L erlenmeyer flask for 15 minutes.
2) 0.752 g PVA (Polyvinyl alcohol, with a degree of polymerisation of 2000 and a degree of hydrolysation of 86-89 mol %, from Fluka Chemika) was weddet with 5 mL methanol and dissolved 130 mL milli-Q water. 100 mL Esperase solution (HPF from Novozymes) was dialysed and freeze dried. There was obtained 6.279 g dry enzyme, which was dissolved quickly (about 5 minutes) in the PVA solution and the obtained viscous enzyme solution was added drop wise to 1) during mixing. The solution was mixed for 15 minutes additionally.
3) 0.517 g of ammonium hydroxide (28-30% solution from Bie & Berntsen) dissolved in 3.737 g of milli-Q water was added dropwise to 2) during mixing at full speed (1500 RPM) on the magnetic stirrer. After additionally 2 minutes of mixing, the white opaque solution was transferred into a 1 L bluecap bottle. After 15 minutes the gelation took place and the obtained 200 mL gel was aged in methanol, for 24 hours at room temperature and additionally 6 days at 5° C., before drying.

4) 176.8 g of the wet gel from 3) was cut into smaller pieces and transferred under methanol to a ½ L pressure vessel (½ L flow reactor, equipped with heating jacket and metal frits in both ends, from Thar designs). There was flowed with L of methanol at 0.5 mL/min. Then the temperature in the heating jacket was raised to 50° C. and the pressure raised to 100 bars, at a rate of 3 bars/min. During 8 hours at 50° C. and 100 bars, 2½ kg of $CO_2$ was flowed trough the vessel at a rate of 5-7 mL/min measured at 10° C. After flowing the pressure was slowly released during several hours. The weight of the supercritical dryed aerogel was 18.685 g.

Example 7

Enzymes Incorporated in a Silica Gel Structure for Water Based Paints 1) 3.82 g TMOS (Tetramethyl orthosilicate 98% from Aldrich) and 20.03 g Properase solution (Properase 1600 L from Danisco) was mixed on a magnetic stirrer in a 100 mL erlenmeyer flask for 15 minutes.
2) 0.1368 g of ammonium hydroxide (28-30% solution from Bie & Berntsen) dissolved in a mixture of 1.02 g of milli-Q water and 4.01 g of PG (Propylene glycol 98% from Fluka), was added dropwise to 1) during mixing at full speed (1500 RPM) on the magnetic stirrer. A transparent orange-brown gel was formed after additionally 50 seconds of mixing.

After aging for 24 hours the gel seems more opaque. The gel was stored in refrigerator at 5° C. until it was used for preparation of a water-based paint. No syneresis was observed.

Example 8

Enzymes Incorporated in a Polymer Reinforced Silica Aerogel for Water-Based Paints 1) 4.68 g TEOS (Tetraethyl orthosilicate 98% from Fluka), 1.00 g of milli-Q water and 1.00 g of a 0.1 M hydrochloric acid solution was mixed on a magnetic stirrer in a 100 mL erlenmeyer flask for 15 minutes.
2) 1.46 g of a 5% (w/w) solution of PVA (Polyvinyl alcohol, with a degree of polymerisation of 2000 and a degree of hydrolysation of 86-89 mol %, from Fluka Chemika) was mixed with 3.98 g PG (Propylene glycol 98% from Fluka) and 13.66 mg ammonium hydroxide (28-30% solution from Bie & Berntsen). The mixture was added dropwise to 2) during continuously stirring. After additionally 2 minutes of mixing pH was measured with indicator paper (from Toyo Roshi Co, Ltd) to be between 5.0 and 5.5.
3) 12.5 mL properase solution (Properase 1600 L from Danisco) was added slowly during mixing and mixing was allowed to proceed for additionally 15 minutes.
4) 12 mL ammonium hydroxide (28-30% solution from Bie & Berntsen) was dissolved in 2 mL of milli-Q water and added dropwise to 3) during mixing at full speed (1500 RPM) on the magnetic stirrer. After additionally 2 minutes of mixing at full speed, the obtained transparent orange-brown sol was transferred into a 100 mL bluecap bottle.

After 7 minutes the gelation took place and the obtained 25 mL orange-brown gel was still transparent after 24 hours aging at room temperature. The gel was stored in refrigerator at 5° C. until it was used for preparation of a water-based paint. Only very little syneresis seems to take place during aging and storing.

Example 9

Aerogels Including Enzymes, Bacteriophages and/or Other Active Components in a Water-Borne Coating 1) Water-Borne Antifouling Composition In water borne paints the inorganic aerogels have until now been of little use. It has been observed that in polishing water-borne paints the aerogel increases the water uptake, reduce hardness and thus may increase the rate of polishing to a level unacceptable for commercial vessels and fast sailing pleasure boats.

In this case an aerogel with a polymer included was introduced into a water-borne yacht paint composition.

| Component | Amount in weight-% |
|---|---|
| 1. Propylenglycol (co-solvent) | 10 |
| 2. Water | 10 |
| 3. Orcrtan 850 EL, 30% (dispersion agent) | 1.4 |
| 4. TEA (amine) | 0.2 |
| 5. Aerogel AP50 | 1 |
| 6. Zinkoxide Code 620 (pigment) | 43 |
| 7. Micro-talc A.T. 1 (filler) | 5 |
| 8. Lipaton X 6030* (acrylic emulsion) | 5 |
| 9. Synaqua 2070, 53% (alkyd emulsion) | 15 |
| 10. Tribuloxyethylphosphate (coalescing agent) | 0.25 |
| 11. Mn-Hydro-cure 9% (direr) | 0.38 |
| 12. Co-HEX-CEM 10% (drier) | 0.14 |
| 13. Tego 1488 (anti-foaming agent) | 0.2 |
| 14. Water | 5.3 |
| 15. Acrysol RM 825 (thickener) | 3 |
| 13. In-can preservation | 0.14 |
| Totally | 100 |

When comparing the properties of the above composition with a composition without polymer in the aerogel the following results are achieved:
- Water uptake (in artificial sea water) is not increased when increasing the aerogel (with polymer) content from 0.5 weight-% to 1 weight-%
- Water uptake(in artificial sea water) is increased when increasing the aerogel (without polymer) content from 0.5 weight-% to 1 weight-%
- The aerogel in itself increases degradation and thus polishing rate when introduced in the composition
- An aerogel including a polymer reduces the polishing effect to some extent.

This composition contains two binders, where one is degrading (alkyde) and the other is giving hardness (acrylic). The alkyde dispersion can of course be omitted if another binder is included that can contribute to degradation in sea water and thus to the polishing rate. The number of binders can be extended to three or more. The binders can be dispersions containing, alkyde or other polyesters, acrylic/ acrylic copolymers, polyvinylacetate, urethanes, rosins, water-soluble resins etc.

Furthermore, the pigment chosen in this case contributes to the polishing rate. Other choices of pigments could contain other metals as titanium (rutile and/or anatase), iron, manganese, molybdenum, etc. It is also possible to use organic pigments in the composition. Likewise can other fillers, film formers (coalescing agents), co-solvents, thickeners and other additives be used.

The aerogel should be regarded as an additive, where the amount normally will be under 5% and in most cases significantly less than 2%. The reason is that the aerogel introduces a different rheological behaviour of the wet product as well as other mechanical properties of the dry coating.

It should be noted that the dispersion agent is chosen to fit to the pigment in the specific type of paint/coating. In this connection the aerogel can have an impact on the choice and amount of dispersion agent due to a large surface area.

The amount of each component is optimised in the specific composition/formulation.

To make a formulation that have the functionality wanted is thus not only a question of using one or the other binder, pigment etc., but a question of choosing an aerogel which fits for the purpose and dosing the amount of formulated aerogel in the correct amount to achieve the physical parameters and the protection against biological growth needed for the application in question.

The same coating can be produced with a wet gel, see table 1b. Choosing a wet gel has several advantages.
- The raw material itself becomes cheaper as a production step in the gel production process is omitted.
- Dust from the aerogel is avoided in the coating production process.
- The wet gel can be designed for different paint systems using different TABLE 1b

| Component | Amount in weight-% |
|---|---|
| 1. Propylenglycol (co-solvent) | 5 |
| 2. Water | 20 |
| 3. Orotan 850 EL, 30% (dispersion agent) | 1.4 |
| 4. TEA (amine) | 0.2 |
| 5. Aerogel wet, (including an active compund) | 10 |
| 6. Zinkoxide Code 620 (pigment) | 43 |
| 7. Micro-talc A.T. 1 (filler) | 5 |
| 8. Lipaton X 6030* (acrylic emulsion) | 5 |
| 9. Synaqua 2070, 53% (alkyd emulsion) | 15 |
| 10. Tributoxyethylphosphate (coalescing agent) | 0.25 |
| 11. Mn-Hydro-cure 9% (direr) | 0.25 |
| 12. Co-HEX-CEM 10% (drier) | 0.09 |
| 13. Tego 1488 (anti-foaming agent) | 0.2 |
| 14. Water | 0.3 |
| 15. Acrysol RM 825 (thickener) | 3 |
| 13. In-can preservation | 0.14 |
| Totally | 100 |

In this example with a water-borne antifouling composition important physical parameters for the coating film are:
- Polishing rate; is decided by the type of vessel or pleasure boat the product is aimed for. Thus a low polishing rate for ships sailing continuously and a higher polishing rate for the yacht market.
- Water uptake; a water-borne coating should not exceed 20 weight-% of water pick-up when exposed to artificial sea water. A high amount of water in the film reduces hardness and increases the degradation where these effects will reduce the protective period and thus be fatal for the coating. As an example a yacht paint should function for at least one sailing season.
- Hardness; the pendulum hardness should be of the same level as other commercial products used in the application area aimed for.

This type of composition could also be formulated as a matte clear coating to be used either as an anti-fouling coating or as a coating at or above the water line.

2) Water-Borne Architectural Paint For Walls And ceilings

One starting formulation is

| Component | Amount in weight-% |
|---|---|
| 1. Propylenglycol (co-solvent) | 10 |
| 2. Water | 10 |
| 3. Orotan 850 EL, 30% (dispersion agent) | 1.4 |
| 4. TEA (amine) | 0.2 |
| 5. Aerogel AP50 | 1 |
| 6. Zinkaxtde Code 620 (pigment) | 43 |
| 7. Micro-talc A.T. 1 (filler) | 5 |
| 8. Lipaton X 6030* (acrylic emulsion) | 5 |
| 9. Synaqua 2070, 53% (alkyd emulsion) | 15 |
| 10. Tributoxyethylphosphate (coalescing agent) | 0.25 |
| 11. Mn-Hydro-cure 9% (direr) | 0.38 |
| 12. Co-HEX-CEM 10% (drier) | 0.14 |
| 13. Tego 1488 (anti-foaming agent) | 0.2 |
| 14. Water | 5.3 |
| 15. Acrysol RM 825 (thickener) | 3 |
| 13. In-can preservation | 0.14 |
| Totally | 100 |

The binder emulsion and binder emulsion amount is chosen in accordance with the use of the paint. In the same way is the type and amount of pigment and fillers chosen.

Examples of binder emulsions that might be used are styrene-acrylics, acrylic-copolymers, vinyl acetates, vinyl acetate/ethylene, alkyds, PU-alkyds, polyurethanes etc. Also in this case water-soluble polymers can be included in a formulation. Due to environmental regulations it is expected that cosolvents and coalescing agents will be minimized further.

The largest use is expected were anti-bacterial surfaces are needed. This means that making a wall paint for hospitals might include an aerogel with bacteriophages (and/or enzymes) that can reduce the risk in connection with certain deceases. In the same way may designed aerogels with active compounds be used in wet rooms.

3) Water-Borne Wood Stain And Wood Finishes

One starting formulation is:

| Component | Approximate amount in weight-% |
|---|---|
| Binder Primal AC-337 (acrylic emulsion) | 42.0 |
| Dispersion agent Tego 740 W | 0.4 |
| Defoamer Foamex 1488 | 0.2 |
| Water | 35.76 |
| Propylene glycol | 5.0 |
| Filler Microdol 1 | 10.0 |
| Texanol | 1.0 |
| Amine | 0.2 |
| Thickener RM 825 | 0.5 |
| Aerogel, with 5% PEG or PVA and/or active compound(s) | 0.8 |
| Hostatint oxide red E-OR | 4.0 |
| n-can preservation | 0.14 |
| Totally | 100.0 |

A wood stain is basically prepared in the same manner as an architectural paint for walls and ceilings. Very often is an alkyd emulsion used often in combination with an acrylic emulsion. It can also be a hybride binder emulsion, e.g. core-shell technology. Furthermore, the possibility of using water-soluble alkyd resins is available. Alkyd polyurethane emulsions, polyurethane dispersions alone or in combination with acrylic emulsions/water-dilutable polyester resins or self-crosslinking acrylic emulsion among other possibilities can also be mentioned. 2C systems are an option. In this type of composition nano particles may also be present to achieve specific physical properties.

Again a designed aerogel will be necessary to achieve the wanted (slow) degradation over time matching the protection against biofilm and biological growth for the given application. Even though most of the applications on wood is expected to be outdoors there will be specific applications indoors as well (i.e. floors, windows).

4) Water-Borne Roof Composition

The difference in the composition from a wood stain is mainly the choice of binder and pigmentation. But the problem is the same with regard to biological growth. Which means that a designed aerogel with enzyme(s) and/or other active compounds may be used in this type of coating with a slow degradation rate. We would expect that the same type aerogel as for wood stain should be used.

One starting formulation is:

| Component | Approximate amount in weight-% |
|---|---|
| PVA binder Acronal S 300, 50% | 48.0 |
| Water | 14.86 |
| Dispersing agent Tego 740 W | 0.4 |
| Defoamer Tego foamex 1488 | 0.4 |
| Titanium dioxide Kemira RDI-S | 5.6 |
| Filler Talc AT 1 | 1.3 |
| Filler Microdol 1 | 25.0 |
| Texanol | 1.0 |
| Thickening agent RM 825 | 0.5 |
| Aerogel (with 5% PEG/PVA and active compound(s)) | 0.8 |
| Hostatint Black E-BLN | 2.0 |
| In-can preservation | 0.14 |
| Totally | 100.0 |

5) Water-Borne Coatings for Materials that are Intended for Contact with Food

In this case, will the components in the water-borne coating have to be approved of, according to EU regulation at the time being. As bacteroiophages can be used against the *Listeria monocytogenes* bacteria it may also be used against *Salmonella*, which may be of interest in connection with materials in direct as well as in-direct contact with food.

The use could include prints on materials as paper, plastic, metal foils etc.

Furthermore, the use is not restricted to one specific printing method or one specific use of printed matter.

6) Other Water Borne Products

It is expected that the use of aerogels can be extended to floor polishes, glues, lacquers, primers, sealers, anti-graffiti products etc.

It is also expected that aerogels including active compounds can be of interest for coatings used on plastic, concrete and steel. The applications can be both for DIY (do-it-yourself) products as well as for industrial applications.

7) Extending the Practical Use of Water-Borne Coatings

Using aerogels including antifreeze protein might extend the use of water-borne products with regard to application. Being able to apply a product at low temperatures and still get film forming is of great interest as well as being able to extend shelf life at low temperatures.

Example 10

Aerogels Including Enzymes, Bacteriophages and/or Other Active Compounds in a Solvent-Based Coating 1) Solvent-Based Wood Stain and Wood Finishes One starting formulation is:

| Component | Approximate amount in weight-% |
|---|---|
| White spirit | 15.0 |
| Dispersion agent Tego 710 | 0.4 |
| Filler Microdol 1 | 46.0 |
| Binder Alkydal F 681 | 31.8 |
| Thickener Luvogel SA1 | 1.0 |
| Aerogel (with active compound(s)) | 0.8 |
| Drier CoZirk 69 | 2.0 |
| Pigment paste Hostatint Oxide red | 3.0 |
| Totally | 100.0 |

A solvent-based wood stain is typically made with an alkyd binder system. It can also be combined with other binders (eg. Polyesters, modified alkyds, rosins and vegetable oils). Binder hybrids and/or copolymers are also a possibility.

In this case will a designed aerogel with enzyme(s) and/or other active compounds be used in a coating with a slow degradation rate. In the composition especially choice of binders is clearly dependent of the application in question. Industrial coatings differ significantly from do-it-yourself products. High solids products are of course important in future.

Floor compositions are often solvent-based 2C binder systems.

2) Industrial Compositions

Thermoplastic acrylic binders can be used in industrial compositions. Alkyds have in this type of application a short to medium oil length, mainly due to the drying time. Again the binders are often functionalised and can be used with different chemistry and in different combinations. Industrial compositions include products for coil coating and heavy-duty applications.

The use of aerogels in industrial applications is obvious with regard to the rheological properties achieved. Still the choice of active compounds has to be in accordance with the use of the coating.

Example 11

Aerogels Including Enzymes, Bacteriophages and/or Other Active Components in Other Coatings Aerogels may find use in coatings that are dried in another manner than solvent-based or water-borne coatings. Examples are UV (or EB) drying coatings for floors and furniture. Here degradation might not be the purpose, but basically to achieve an antibacterial effect. The drying process can also be a combination of physical drying and radiation.

The invention claimed is:

1. An anti-fouling paint composition comprising an anti-fouling additive comprising:

a) a silica-containing aerogel or a silica-containing cryogel comprising a gel lattice, and optionally comprising a metal alcoxide comprising Sc, Ti, V, Cr, Mn, Fe, Co, Y, Zr, Nb, Ru, Hf, Ta, W, Re, Si, Al, Ge, In, La, Pr, Nd, Sm, Eu, Gd, Tb, Dy, Ho, Er, Tm, Yb or Lu, b) one or more enzymes selected from the group consisting of hemicellulolytically active enzymes, amylolytically active enzymes and/or cellulolytically active enzymes entrapped in said aerogel or cryogel, said enzymes being released from the lattice by degradation of the gel in a controlled manner over time, said aerogel or cryogel having pores of between 1 and 20 nm, and having been manufactured using supercritical extraction, supercritical drying or freeze drying of a corresponding alcogel, the amount of said one or more enzymes being sufficient to impede or reduce the evolution of biofilms on structures to be exposed to sea water, and c) one or more components selected from binders, pigments, extenders, fillers, dispersion agents, and d) optionally $Cu_2O$, ZnO and other paint additives, wherein said anti-fouling additive is present in the paint in an amount being sufficient to impede or reduce the evolution of biofilms on structures to be exposed to sea water.

2. A paint composition according to claim 1 which is water-borne.

3. A paint composition according to claim 1 which is solvent based.

4. A paint composition according to claim 2 which is self-polishing.

5. A paint composition according to claim 4 wherein the structures to be exposed to sea water are pleasure boats, yachts, commercial vessels and other structures exposed to sea water.

6. A paint composition according to claim 4 wherein the structures to be exposed to sea water and/or to high humidity are painted wood structures, houses, roofs and other painted structures placed outdoors.

7. A method for treating a surface of a structure to be exposed to sea water in order to Impede or reduce the evolution of biofilms, comprising mixing from about 95% to about 99.5% by weight of a selected paint base material with from about 0.5% to about 5% by weight of an anti-fouling additive according to claim 1, and applying an adequate amount of the resultant mixture to the surface to be exposed to water to impede or reduce the evolution of biofilms.

8. A method for treating a surface of a structure to be exposed to water in order to impede or reduce the evolution of biofilms, comprising applying to said surface an adequate amount of a paint composition according to claim 4.

9. The anti-fouling paint composition of claim 4 wherein the hemocellulolytically active enzymes are members selected from the group consisting of Endo-I, 4-beta-xylanase (E.C. 3.2.1.8), Xylan endo-1,3-beta-xylosidase (E.C. 3.2.1.32) Glucuronoarabinoxylan endo-1,4-beta- xylanase (E.C. 3.2.1.136), Beta mannosidase (E.C. 3. 2.1.25), Mannan endo-1,4-beta-mannosidase (5 E.C. 3.2.1.78) and Mannan endo-1,6-beta-mannosidase (E.C. 3.2.1.101).

10. The anti-fouling paint composition of claim 4 wherein the amylolytically active enzymes are selected from the group consisting of amylases, amyloglucosidases (E.C. 3.2.1.3), pullulanases, α-1,6-endoglucanases, α-1,4-exoglucanases and isoamylases.

11. The anti-fouling paint composition of claim 4 further comprising a gel.

* * * * *